United States Patent [19]

Lewis

[11] 4,119,095
[45] Oct. 10, 1978

[54] RESTRAINING GARMENT

[76] Inventor: Mattie Lewis, 111 Benicia Rd., Vallejo, Calif. 94590

[21] Appl. No.: 798,565

[22] Filed: May 19, 1977

[51] Int. Cl.² ............................................. A61F 13/00
[52] U.S. Cl. .................................. 128/134; 2/DIG. 7
[58] Field of Search ............ 128/133, 134; 2/DIG. 7, 2/73, 74, 114

[56] References Cited

U.S. PATENT DOCUMENTS

| | | | |
|---|---|---|---|
| 2,707,282 | 5/1955 | Paterson | 2/DIG. 7 |
| 2,846,686 | 8/1958 | Tames | 2/DIG. 7 |
| 3,407,807 | 10/1968 | Giberson | 128/134 |
| 3,720,957 | 3/1973 | Patience | 2/DIG. 7 |
| 4,026,282 | 5/1977 | Thomas | 128/134 |

Primary Examiner—Lawrence W. Trapp
Attorney, Agent, or Firm—Warren, Chickering & Grunewald

[57] ABSTRACT

A restraining garment that is both physically and psychologically comfortable which includes a yoke having head and arm holes and an elongated front portion that contains an expanded element such as a large gusset with the front portion sewed to the yoke and tunnel-like elements for holding a restraining belt with the tunnel-like elements positioned to encircle the chest cage of a patient whereby no pressure is brought against a tender abdomen and the restraining belt is invisible within the tunnel element so that a patient is unaware that he is being restrained.

3 Claims, 3 Drawing Figures

RESTRAINING GARMENT

BACKGROUND OF THE INVENTION

It is well known that patients frequently need to be restrained. Restraint of patients occurs under a number of conditions. One of the most frequent needs for restraint is for a post-surgery patient whose mental facilities are diminished because of anesthetic and shock. It is important that post-surgery patients be maintained in bed and frequently in a specific position, such as lying on their backs, and such patients frequently have abdominal incisions that are very tender. Another frequent need for restraint is in patients having psychiatric disorders. Many psychiatric disorders, particularly psychiatric disorders involving alcoholism, produce very tender abdomens. Patients requiring constant or at least prolonged restraint having tender abdomens frequently must endure much pain because of the restraint. Another frequent use of restraints is with elderly or spastic patients where they must be restrained more in sitting positions than in lying positions. Restraints for such patients must be relatively tight to keep the patient from slumping within the supporting chair. It is desirable for such restraints to be positioned so that circulation is not cut off or to prevent constant pressure against tender organs.

Post-operative patients and psychiatric patients frequently react with some emotional panic to restraints. To avoid emotional problems, it is desirable to use a restraint that does not look like a restraint. For example, a restraint that would look like an ordinary garment or a hospital bed jacket would be accepted by a patient who is not fully mentally aware as an ordinary item of clothing rather than a restraint.

THE INVENTION

This invention is a restraining garment that avoids or greatly mitigates all of the above noted problems. The restraining garment of this invention includes a front yoke that is preferably fairly deep and contains or at least forms a portion of openings for the head and arms of a patient. The yoke also contains or it forms at least a portion of shoulder engaging elements. The garment can be in the form of a vest or it can have sleeves when desired.

The front portion of the garment is sewed to the yoke. The front portion includes an expandable element which is also sewed to the yoke. The expandable element is capable of increasing the effective width of the front portion of the yoke by a substantial degree with very small force needed. The preferred expandable portion is a deep gusset that extends from the yoke to the bottom of the front portion, which gusset can be loosely laid upon the abdomen of a patient exerting no more force on the abdomen than the force of gravity. Another suitable expandable element is an elastic inset. When an elastic inset is employed, it should be made of a material that requires very small force to expand so that pressure on the abdomen of a patient is avoided. The front portion of the garment also includes two tunnel elements, one on each side of the expandable element. The tunnel elements are adapted to contain a belt and hold it in a fixed position on the front portion of the garment. The tunnel elements are spaced from the yoke such that when the garment is on a patient the tunnel elements will engage the patient around the chest cage, preferably at a level about at the sternum.

The garment of this invention also includes a back portion which includes appropriate closure means to hold the garment appropriately on the patient.

DETAILED DESCRIPTION OF THE INVENTION

The restraining garment of this invention can best be described with reference to the accompanying drawings.

Figure 1:
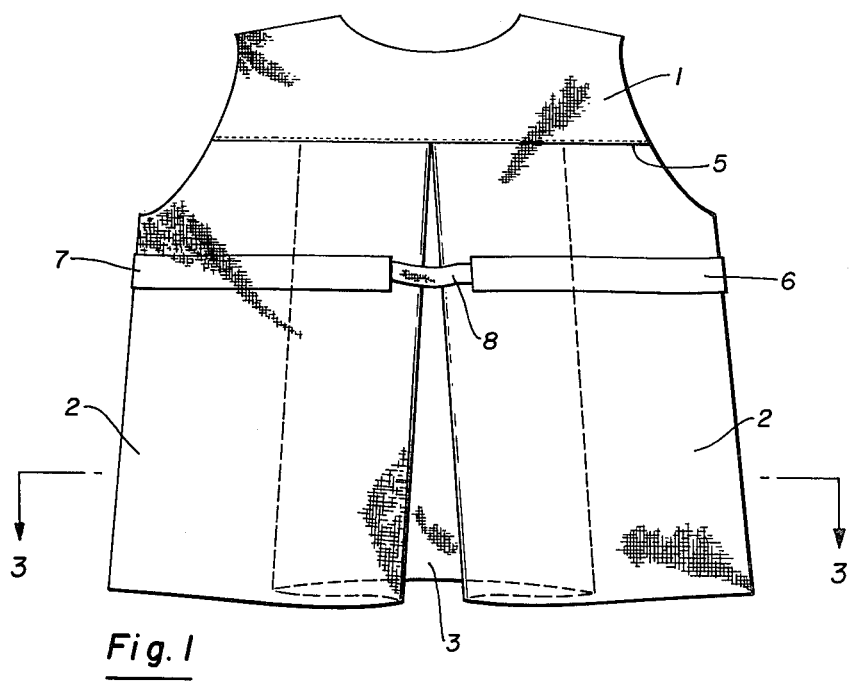
FIG. 1 is a view of the front of a garment embodying this invention.

The embodiment of the invention illustrated in the accompanying figures is a garment in the form of a vest. The garment includes a front yoke 1 and a front portion 2 which includes an element on either side of an expandable portion 3. The front portion is held to the yoke by a seam 5. The expandable portion illustrated in the drawings is a deep gusset which extends all the way up to and is sewn into the seam 5.

Figure 2:
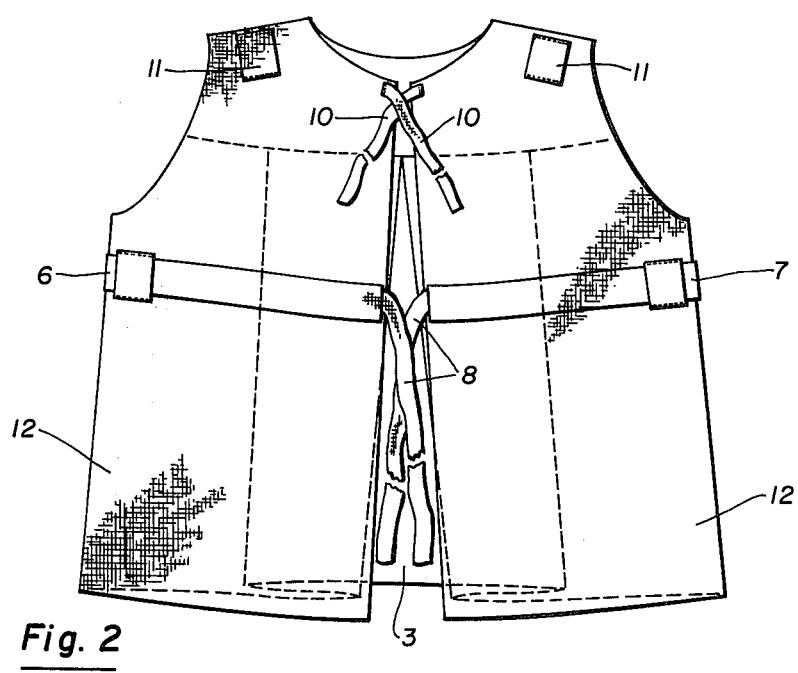
FIG. 2 is a view of the back of a garment embodying this invention.
Figure 3:
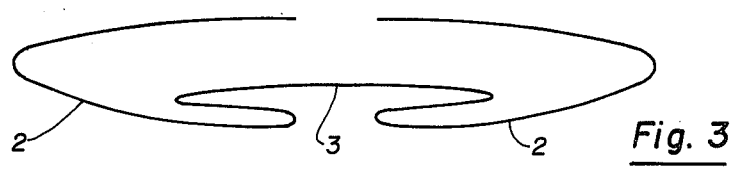
FIG. 3 is a section view of the garment illustrated in FIG. 1 taken along the line 3—3.

The front portion 2 is also provided with two tunnel elements 6 and 7. The tunnel elements are in the form of elongated belt loops and contain within them a belt 8. Tunnel elements 6 and 7 are spaced from the portion of the yoke 1 that engages the shoulders of a patient such that a patient wearing the garment illustrated herein in the normal manner will have the belt 8 encircling his chest cage rather than his abdomen. Tunnels 6 and 7 may encircle the garment and open around the back as illustrated in FIG. 2 or they may terminate at the sides of the garment. The back of the garment is provided with normal closure means such as tapes 10 which permit the garment to be closed around the patient without using a hard or uncomfortable element such as a zipper or a button. The rear portion of the garment up near the shoulders may also be provided with belt loops 11 which may be useful for holding a patient's shoulders against a chair so that a patient restrained in a chair may be maintained in an upright position. The back portion of the garment 12 may be made of the same piece of fabric as the front portion or it may be sewed to the front portion along side seams. Although any suitable material may be employed to make the restraining garment of this invention, it is preferred that the garment be made of heavy, washable white fabric such as duck.

In use, the garment is placed on a patient much like any hospital gown. The patient's arms are placed through the arm holes and tapes 10 are tied in a bow so that the garment is closed around the back of the patient. The garment is pulled down comfortably and the patient is then placed in a reclining position. The belt 8 is then tied to the bed on which the patient is lying to secure the patient from rolling off the bed or sitting up. From the patient's point of view, he is wearing an ordinary hospital gown. The belt is completely hidden in the tunnel element and the tunnel elements are high enough on the torso of the patient so that they are not readily visible. The restraint is around the rib cage and only loose fabric exerting the force of its own weight is aroung the abdomen. The gusset 3, which is normally the same piece of fabric as the garment front 2, is folded back on itself between 8 and 12 inches so that the gusset is capable of expanding from 16 to 24 inches before any tightness will be felt about the abdomen. Normally, the front pieces 2 will be together at the position where tunnel elements 6 and 7 meet. However, when a patient has a particularly swollen abdomen, it may be necessary to separate the gusset slightly where tunnel elements 6 and 7 meet to ensure that there will be no stretched fabric over the abdomen. This aspect is particularly important for patients suffering from acute alcoholism where the abdomen is particularly tender, where the abdomen frequently is distended to an exaggerated degree and where patients are inclined to struggle against restraints. When it is desired to add further insurance that the expandable element will not cause discomfort to a patient, a gusset may be made from a separate, more elastic material so that even in its most extended position or when a patient struggles against it, it will provide some degree of yielding to avoid discomfort to the patient.

The foregoing description describing the particular embodiment of this invention illustrated in the drawings is intended to be illustrative of the invention rather than limiting on its scope. Many garments with different constructions may be made within the broad concept of this invention.

What is claimed is:

1. A restraining garment comprising a front yoke including at least a portion of a head opening, arm openings and shoulder engaging portions, a front portion including an expandable element, said front portion and said expandable element being sewn to said yoke, two tunnel elements sewn to said front portion to traverse said front portion but not sewn to said expandable portion, said tunnel elements spaced from said shoulder engaging elements to encircle the chest cage of a patient wearing said garment, a back portion including closure means for said garment, and a belt passing through said tunnel elements.

2. The restraining garment of claim 1 wherein said expandable element is a gusset.

3. The restraining garment of claim 1 wherein said expandable element includes an elastic portion extending from said yoke to the bottom of said front portion.

* * * * *